United States Patent
Kawasumi

(10) Patent No.: US 9,782,234 B2
(45) Date of Patent: Oct. 10, 2017

(54) ATTACHMENT FOR STETHOSCOPE

(71) Applicants: WING Co., Ltd., Ikoma-shi (JP);
Earth Create Co., Ltd., Nara-shi (JP)

(72) Inventor: Ryohei Kawasumi, Ikoma (JP)

(73) Assignees: WING Co., Ltd., Ikoma-shi (JP);
Earth Create Co., Ltd., Nara-shi (JP)

( * ) Notice: Subject to any disclaimer, the term of this patent is extended or adjusted under 35 U.S.C. 154(b) by 0 days.

(21) Appl. No.: 15/103,863

(22) PCT Filed: Nov. 28, 2014

(86) PCT No.: PCT/JP2014/081504
§ 371 (c)(1),
(2) Date: Jun. 11, 2016

(87) PCT Pub. No.: WO2015/087713
PCT Pub. Date: Jun. 18, 2015

(65) Prior Publication Data
US 2016/0324594 A1 Nov. 10, 2016

(30) Foreign Application Priority Data
Dec. 12, 2013 (JP) .................. 2013-257494

(51) Int. Cl.
- *A61B 7/00* (2006.01)
- *A61B 90/57* (2016.01)
- *A61B 7/02* (2006.01)

(52) U.S. Cl.
CPC ............... *A61B 90/57* (2016.02); *A61B 7/00* (2013.01); *A61B 7/02* (2013.01); *A61B 2560/0443* (2013.01)

(58) Field of Classification Search
CPC .. A61B 7/00; A61B 7/02; A61B 90/57; A61B 2560/0443
(Continued)

(56) References Cited

U.S. PATENT DOCUMENTS 717,898 A * 1/1903 McCully ............. H04R 25/652
181/135
4,406,346 A * 9/1983 Pope, Jr. .................. A61B 7/02
181/131
(Continued)

FOREIGN PATENT DOCUMENTS

CN 201920756 U 8/2011
JP 04-108512 U 9/1992
(Continued)

OTHER PUBLICATIONS

International Search Report mailed Feb. 10, 2015, issued for PCT/JP2014/081504.

*Primary Examiner* — Forrest M Phillips
(74) *Attorney, Agent, or Firm* — Locke Lord LLP

(57) ABSTRACT

Upon using a stethoscope, there is a problem that it had been needed to interrupt work and mount the stethoscope using both hands, resulting in poor work efficiency. Also, when it is needed to repeatedly mount and unmount the stethoscope for such as a group examination, for example, it had been necessary to continuously carry out an operation of expanding ear tubes many times, which is complicated. Thus the present invention provides an attachment for a stethoscope comprising a mounting part which can be mounted to both of ear tubes, and a manipulating part for manipulating the mounting part, the manipulating part and the mounting part being connected through a rotatable fulcrum, so that the mounting part may be opened and closed by opening and closing operation of the manipulating part.

14 Claims, 7 Drawing Sheets

(58) Field of Classification Search
USPC .......................................................... 181/131
See application file for complete search history.

(56) References Cited

U.S. PATENT DOCUMENTS

| | | | | |
|---|---|---|---|---|
| 5,466,898 | A * | 11/1995 | Gilbert | A61B 46/10 181/131 |
| 5,847,330 | A * | 12/1998 | Grosslight | A61B 7/02 181/131 |
| 6,883,639 | B1 * | 4/2005 | Lam | A61B 7/02 181/131 |
| 8,037,965 | B1 * | 10/2011 | Swink | A61B 7/02 181/131 |
| 2010/0307860 | A1 * | 12/2010 | Ellingson | A61B 7/02 181/131 |
| 2011/0088964 | A1 * | 4/2011 | MacMackin | A61B 7/02 181/131 |

FOREIGN PATENT DOCUMENTS

| | | |
|---|---|---|
| JP | 2013-192919 A | 9/2013 |
| JP | 5512875 B1 | 6/2014 |

\* cited by examiner

ATTACHMENT FOR STETHOSCOPE

TECHNICAL FIELD

The present invention relates to an attachment for stethoscope to be attached to a stethoscope.

BACKGROUND ART

Conventionally, there has been provided a stethoscope which is used by doctors, nurses, etc., and comprises a sound collection unit for detecting the auscultation sounds and an ear tube, which is branched into a left-side tube portion and a right-side tube portion so as to be inserted into the left and right ears of a user, and the left-side tube portion and the right-side tube portion being connected by use of a connecting pipe, such as a rubber pipe. In such stethoscope, when the doctor or the like who is the user puts on the stethoscope, it is required such manipulation (expansion operation) that an external force is applied to the ear tube, (i.e., the left-side and right-side tube portions in a state of being close to each other with the elastic force of the ear tube itself), in the direction of expanding the interval between the left tube portion and the right tube portion. Therefore, for putting on the stethoscope, it is necessary for the doctors or the like as a user to use both hands.

Hereat, in the practical medical field, despite the need to perform various tasks, there is a problem in use of the stethoscope that it is required to stop the work once and to put on the stethoscope with both hands, leading to a poor working efficiency. Further, for example, in the case for a group medical examination as attachment and detachment of the stethoscope must be repeated, it is necessary and troublesome to carry out the foregoing expansion operation of the ear tube continuously many times. Thus, if it is realized to attach and detach the stethoscope only with one hand, while any necessary work being kept with other hand, further improvement of the work efficiency in the medical field can be expected. Reviewing from such a viewpoint as above-mentioned, for example, it may be effective the TMJ stethoscope for screening as disclosed in Patent Document 1.

CITATION LIST

Patent Literature

Patent document 1: Japanese Unexamined Patent Application NO. 2013-192919

Patent document 2: U.S. Pat. No. 8,037,965

SUMMARY OF INVENTION

Technical Problem

Here, the temporomandibular joint stethoscope for the screening described in Patent Document 1 mentioned above discloses that a spring loaded gripping means is provided onto the ear tube portion the examiner puts on, so that the examiner can put on the ear tube portion with one hand (see claim 4 of the Japanese unexamined patent application No. 2013-192919). But, the spring loaded gripping means of the invention of this prior art is not able to be retrofitted to the ear tube portion. Moreover, the spring loaded gripping means of the prior art invention is not envisaged to be retrofitted to existing stethoscopes and does not have any consideration for the purpose. Thus, it cannot be attached to existing stethoscopes such as those customarily used by a doctor etc., and it is not usable well. Stethoscopes are normally used being put on users' (doctors, etc.) bodies, thereby different or separate stethoscopes may be used possibly depending upon users preferences, specific use, or the like. Hence, it is desired strongly provision of attachments which being able to be mounted to any existing or freely selected stethoscopes and usable without problems.

An expanding device for stethoscopes disclosed in the patent document 2 does, as apparently seen from FIG. 1, comprise a first member and a second member which are formed in a large round shape and protrudes upward than the branching portion of the connection tube described later. The members hit against or get in the way carrying the jaw of the user. To avoid this, the branching portion of the connection tube must be positioned as largely lowered downwards, thus, commercially available stethoscopes cannot be applied.

The present invention may, as mentioned foregoing, employ those of the ordinary stethoscopes selected by doctors (physicians, etc.) according to their own preferences and specific use.

In order to solve the above-mentioned problems, the present invention has an object to provide an attachment for stethoscope which may be attached to any freely selected stethoscopes, enabling the ear tube to be operated without the problems.

Solution to Problem

In view of the situation as above-mentioned, the present inventor's having conducted extensive studies have completed the present invention which:

an attachment 10 for a stethoscope which to be mounted to a stethoscope 1 comprising:

a sound collecting unit 2 for detecting the auscultation sounds, ear tube 3 branched into a left tube part 3*a* and a right tube part 3*b* so as to be inserted into the left and right ears of a user, and a connecting pipe 4 which connects the sound collecting unit 2 and the left tube part 3*a* and the right tube part 3*b*, wherein an elastic force of the connecting pipe 4 urges the left tube part 3*a* and the right tube part 3*b* in a direction that the parts 3*a* and 3*b* become close to each other through the connecting pipe, so that there can be applied an external force in the opposite direction to the urging direction against the left tube part 3*a* and the right tube part 3*b*, or one ends of the left tube part 3*a* and the right tube part 3*b* covered with ends of the connecting pipe 4 at the side of the ear tube 3 to provide an expansion state in which the left tube part 3*a* and the right tube part 3*b* are allowed to elastically deform and the interval of the left tube part 3*a* and the right tube part 3*b* expands, characterized in that the attachment 10 for stethoscope 1 comprises: a mounting part 20 to be mounted onto the ear tube 3 and a manipulating part 22 for manipulating the mounting part 20, the manipulating part 22 and the mounting part 20 are connected through a rotatable hinge 18, so that the mounting part 20 may be opened and closed by opening and closing operation of the manipulating part 22, and upon the attachment's being fit onto the stethoscope the hinge is positioned outside a region surrounded by the left tube part 3*a* and the right tube part 3*b*, and the connecting pipe 4.

The attachment for stethoscope of the present invention enables that the mounting parts of the left and the right manipulation parts are each freely attached to or detached from the left and the right tube parts, respectively. Thus, the attachment for stethoscope of the present invention may be mounted for use to any stethoscopes freely selected by doctors, etc., with their preferences. And the attachment for stethoscope may be operated merely for causing the manipulating parts of the left and the right manipulation parts to approach with each other, so that the interval between the left and the right tube parts is expanded interlocking with the movement of the mounting part of the left manipulation part and that of the right manipulation part. By this, according to use of the attachment for stethoscope of the present invention, doctors, etc., are enabled to expand the interval between the ear tubes with their single hand operation and fit the ear tubes to ears. Hence, use of the attachment for stethoscope of the present invention can notably improve work efficiency of the doctors, etc.

Furthermore, in the attachment for stethoscope of the present invention, any one or both of the mounting part(s) of the left manipulation part and the right manipulation part may be, preferably, attached in a manner of being capable of sliding along the left tube part or the right tube part.

With the structure as above-mentioned, it is realized that upon the expansion operation, the mounting part may be caused to slide along the left or the right tube part, whereby, a load required for the expansion of the interval between the left and the right tube parts of the ear tube can be lowered. Thus, according to the present invention, there has been provided such attachment for stethoscope that the expansion operation for bringing the ear tube into the state of interval expansion can be carried out more lightly.

The above-mentioned stethoscope attachment of the present invention may be so structured that one or both of the mounting parts of the left manipulation part and the right manipulation part is/are mounted by use of amounting member fit winding outer peripheries of the mounting part together with the left or the right tube part.

With this structure, there has been provided such stethoscope attachment that the left tube part and the right tube part are ensured to be brought into the expansion state interlocking with the expansion operation by the left or right manipulation part.

The above-mentioned attachment for stethoscope of the present invention may be so structured that the attachment comprises an annular member for mounting one or both of the mounting parts of the left and the right manipulation parts to the left tube part or the right tube part, the mounting part is provided with an insertion part through which the annular member is able to be inserted through, so that the annular member inserted through the insertion part may be fit and wound on the left and the right tube parts, whereby mounting one or both of the mounting parts of the left and the right manipulation parts to the left tube part or the right tube part.

The hinge referred to in the present invention is a part where any members are connected in a manner of being able to rotate. The hinge should not be limited in shape and structure to any ones particularly. It may employ a hinge of such structure that members intersecting each other have a through bore through which a shaft member is merely inserted.

A big point of the present invention is that the hinge section, when the attachment is mounted to the stethoscope, is positioned outside the region surrounded by the left tube part 3a, the right tube part 3b and the connecting pipe 4. In other words, when the manipulating part is manipulated to narrow the interval between the manipulation part sections, the hinge part is moved upwards, and the hinge part even at this fresh position is positioned outside that region.

By this feature, the hinge part does not strike jaw and neck of users and not hinder them.

A stopper to prevent more than a predetermined extent of narrowing of the interval between the left and the right manipulation parts may be provided at the hinge part of the present invention. In detail, the left and the right manipulation parts in the stethoscope are in the state of being in proximity to each other due to an elastic force of the stethoscope itself. In case that the left and the right manipulation parts approach each other more than required, the left and the right manipulation parts get caught and troublesomely when in expansion operation. Thus, the hinge may be provided with a stopper for retaining and stopping the hinge in the midst of rotation so as to prevent lowering of interval of the manipulation parts more than required (a level of proximity more than that the ear tubes precisely fit into users ears).

When structured as the above-mentioned feature, the left manipulation part and the right manipulation part are enabled to be more surely mounted to the left tube part and the right tube part of the ear tube. By this, it is enabled that the interval between the left tube part and the right tube part is expanded surely interlocking with the movement of the left manipulation part and the right manipulation part in the expansion operation. Hence, according to the present invention, the left manipulation part and the right manipulation part are enabled to be more surely mounted to the left tube part and the right tube part of the ear tube, and also, certainty of the ear tube's movement of expansion in the expansion operation can be facilitated.

Advantageous Effects of Invention

According to the present invention, it is provided an attachment for stethoscope which may be mounted to any desired stethoscope to be able to manipulate ear tubes without any problems.

DESCRIPTION OF EMBODIMENTS

First Embodiment

Hereinafter, explanation will be given regarding the attachment 10 for stethoscope according to the first embodiment of the present invention. In the following description, prior to the explanation of the stethoscope attachment 10 of this embodiment, a schematic configuration of a stethoscope 1 to which the invention is attached will be first explained. In the following description, unless otherwise specified, explanation will be given using positional correlation of the left and right and front and back sides with the state of the stethoscope 1 as arranged and shown in FIG. 1 being taken as a reference.

(A Schematic Configuration of Stethoscope 1)

Figure 1:
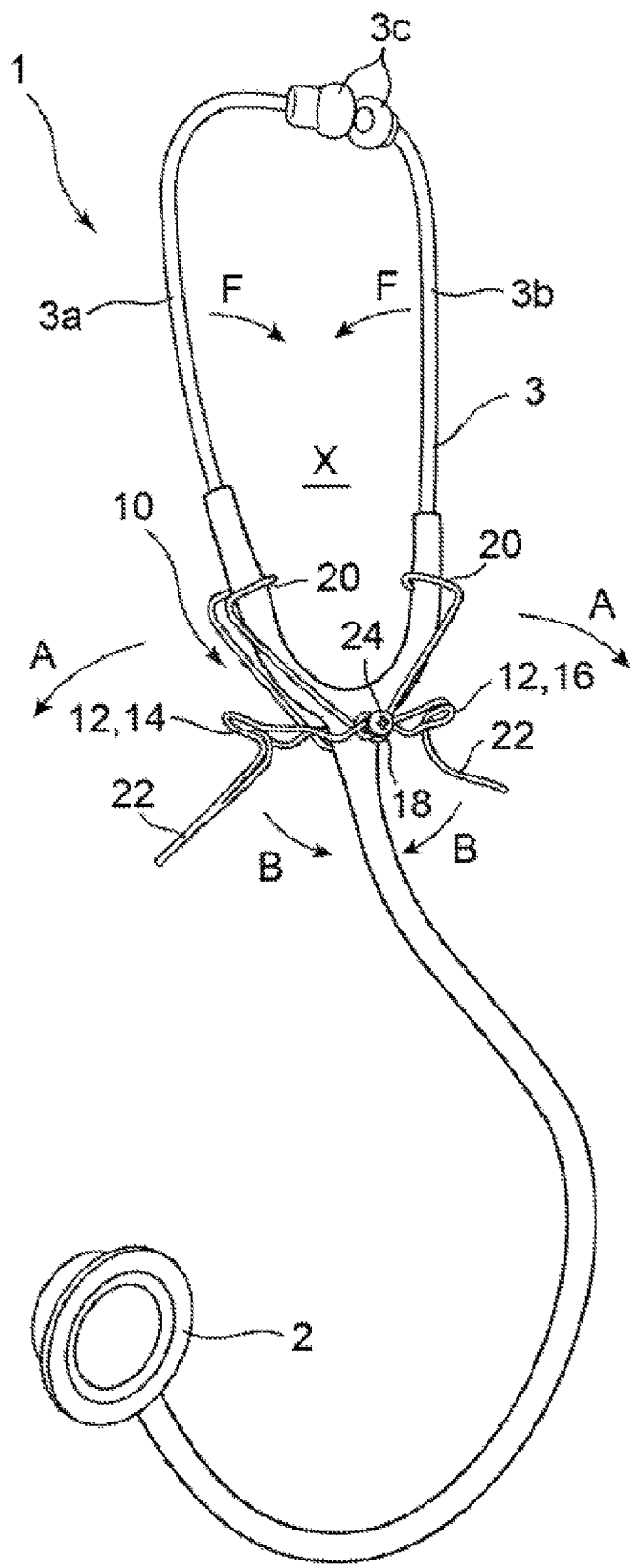
FIG. 1: a perspective view showing an example of an attachment for stethoscope according to the present invention in the state of being mounted to the stethoscope.

As shown in FIG. 1, the stethoscope 1 has a sound collecting unit 2, an ear tube 3, and a connecting pipe 4. The sound collecting unit 2 is a part provided for detecting the auscultation sound by contacting with a target of sound collection such as a human body.

Ear tube 3 comprises a tubular body made of a metal tube or the like and is shaped as being curved to be capable of being inserted into left and right ears of a user such as a doctor. The ear tube 3 is branched into left and right tube parts 3a and 3b and mounts ear pieces 3c at the utmost ends which to be inserted into user's ears. The ear tube 3 is urged, by the elastic force of itself, into the direction in which the left and the right tube parts 3a and 3b become close to each other (arrow F direction in FIG. 1). By applying an external force to the ear tube 3 in the opposite direction (the arrow A in FIG. 1) to the foregoing urging direction, the ear tube 3 can be brought into the state that the interval between the left tube part 3a and the right tube part 3b is expanded (the expansion state). Users of the stethoscope 1 may have to only cause the ear tube 3 to be in the expansion state, that is, merely expanding the interval of the ear tube 3 widely in comparison with the interval between their both ears, so that the ear pieces 3c can be inserted into users both ears and put on.

The connecting pipe 4 is a pipe to connect the sound collecting unit 2 and the ear tube 3. The connecting pipe 4 is formed with a pipe having high bendability made of a rubber pipe or a plastic pipe such as vinyl chloride. The connecting pipe 4, at the section extending between the sound collecting unit 2 and the start part of branching into the left tube 3a and right tube 3b of the ear tube 3, may be properly formed with: a single pipe, or, a single pipe having an inside partition wall; or, two pipes. Moreover, the connecting pipe 4 at the end at the side of the ear tube 3 partially covers the part of the left tube 3a and the right tube 3b (forming the ear tube 3) at their base ends (opposite to the side of ear piece 3c).

(Regarding Attachment 10 for Stethoscope)

Figure 2:
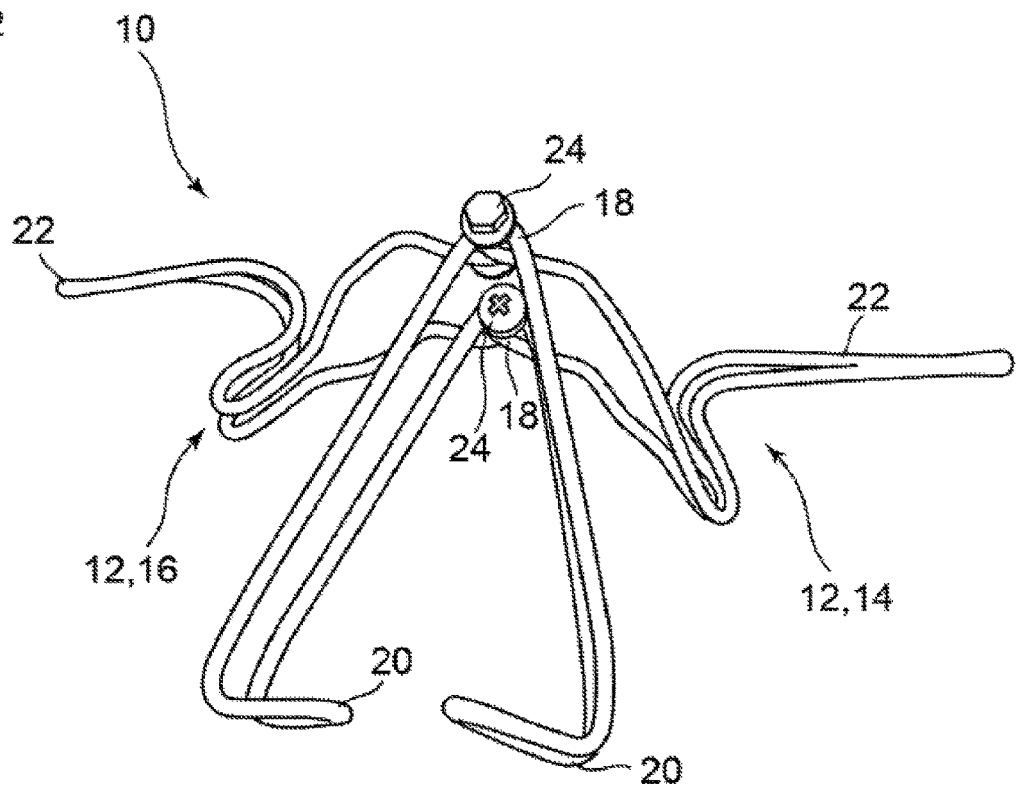
FIG. 2: a perspective view showing an example of an attachment for stethoscope according to the present invention.

As shown in FIG. 1, the attachment 10 for stethoscope is an attachment to be mounted to the above-mentioned stethoscope 1 to enable the operation for bringing the ear tube 3 into the expansion state. As seen in FIGS. 1 and 2, the stethoscope attachment 10 comprises a pair of manipulation units 12 (each also called hereunder when required a left manipulation part 14 and a right manipulation part 16) and a hinge 18.

The manipulation unit 12 (left manipulation part 14 and right manipulation part 16) is so structured as having a mounting part 20 at one end and a manipulating part 22 at the other end. The manipulation unit 12 is formed by working a wire material (such as wire) into a shape of bending. The left and the right manipulation parts 14 and 16 are in a shape of substantially symmetric with each other.

The left and the right manipulation parts 14 and 16 can be each mounted (at the mounting part 20) to and detached from the left tube 3a and the right tube 3b, respectively. In detail, the mounting part 20 is in a shape of a hook bending along the outer peripheries of the left tube 3a and the right tube 3b. The mounting part 20 can be mounted to the left tube 3a and the right tube 3b in a manner of catching the left tube 3a and the right tube 3b in the direction extending outwardly from the region X defined (inside) by the left tube 3a and right tube 3b. In the present embodiment, the mounting part 20 of the left manipulation part 14 and the right manipulation part 16 are mounted to the sections of the left tube 3a and right tube 3b at their base ends covered with the connecting pipe 4 made of rubber or the like. Thus, the mounting parts 20 are mounted to the connecting pipe 4 in a manner of not easily falling thanks to a frictional force occurring between the connecting pipe 4 and the mounting parts 20.

The manipulating part 22 is formed on the manipulation unit 12 at the side opposite to the mounting part 20. The manipulating part 22 is a part to be caught by users fingers upon manipulation of the attachment 10 for stethoscope. In detail, one of the manipulating part 22 of the left and the right manipulation part 14 and 16 is caught, for example, by thumb or the like of users hands, and the other manipulating part 22 caught by forefinger or the like of users hands. And users holding movement with fingers (as shown by the arrow B in FIG. 1) to cause the fingers (holding the manipulating parts 22 of the left and the right manipulation parts 14, 16) to approach each other enables performance of the operation for moving the left and the right manipulation parts 14, 16 in the direction shown by the arrow A in FIG. 1.

The hinge 18 is provided at an intermediate position between the mounting part 20 of the left and the right manipulation parts 14, 16 and the manipulating part 22 and connects the left and the right manipulation parts 14 and 16 in a manner of enabling the same to be operated opened and closed. In this embodiment, the hinge 18 is formed in such manner that a fulcrum shaft 24 made from a combination of bolt and nut or the like is inserted through a hole-like part provided by looping a wire material which forms the left manipulation part 14 and the right manipulation part 16. Furthermore, in this embodiment, the hinge 18 is provided at both sides, namely, the front side and the back side of the stethoscope attachment in the state of being mounted to the stethoscope 1.

The stethoscope attachment 10 functions such that the manipulating parts 22 are held by users with their fingers (as shown by the arrow B in FIG. 1) to cause the manipulating parts 22 of the left and the right manipulation parts 14, 16 to approach each other, thereby enabling expansion of the interval between the mounting parts 20 of the left and the right manipulation parts 14, 16 shown by the arrow A in FIG. 1. By this, such manipulation (expansion operation) is enabled that an external force is applied to the left tube part 3a and the right tube part 3b to expand the interval between the tube parts 3a, 3b. Hence, the stethoscope attachment 10 may be used, by users such as doctors or the like, to enable them to expand the interval of the ear tube 3 with manipulation using a single hand and put the ear tube to the ear. Moreover, when users stop holding the manipulating part 22 with their fingers, the ear tube 3 returns to its original state thanks to the own elastic force of the ear tube 3. Thus, user applies the ear tube 3 (whose interval has been expanded in the direction of the arrow A with the expansion operation) to ears, thereafter, merely stops holding the manipulating part 22 with their fingers, so that putting on the stethoscope 1 completes. Also, when user wants to take off the stethoscope 1, mere manipulation of holding the manipulating parts 22 with their fingers to expand the interval of the ear tube 3 is sufficient for taking off the stethoscope 1.

As above-mentioned, the attachment 10 for stethoscope enables readily putting on and taking off the stethoscope 1 by operating the manipulating part 22 with a single hand. Hence, by use of the attachment 10 for stethoscope, working efficiency of doctors, etc., can be improved remarkably.

Furthermore, the above-mentioned stethoscope attachment 10 may be attached for use to any stethoscopes 1 freely selected by the doctors or the like. Thus, according to the stethoscope attachment 10, with respect to various types of stethoscope 1 selected by the doctors or the like on the basis of their preference, use, or the like, attaching and detaching of the stethoscope attachment 10 can be carried out with a single hand.

Second Embodiment

Hereunder, an attachment 100 for stethoscope according to the second embodiment of the present invention will be explained with referring to an example of mounting to the foregoing stethoscope 1. A structure in the attachment 100 common to the stethoscope attachment 10 of the above-mentioned first embodiment is designated by reference numbers prepared with the original reference numbers in the first embodiment plus 100. And detailed explanation of such structure(s) will be omitted.

Figure 3:
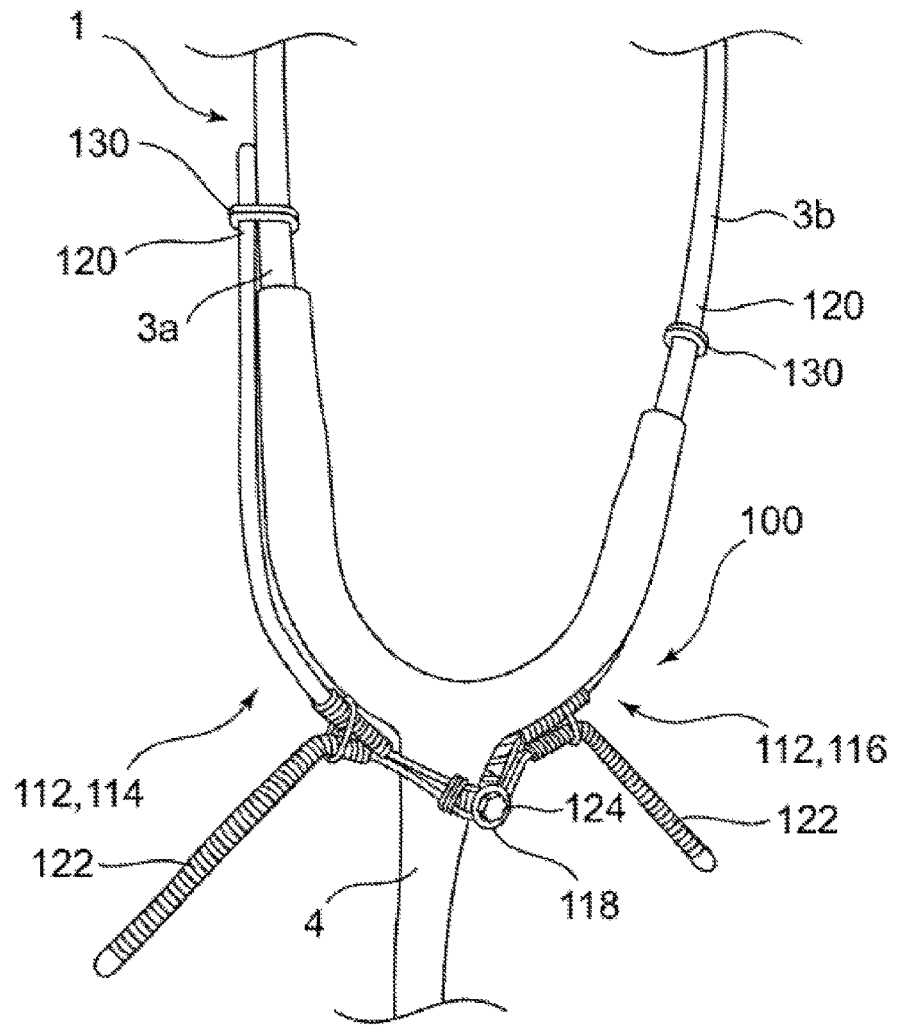
FIG. 3: a perspective view showing another example of an attachment for stethoscope according to the present invention in the state of being mounted to the stethoscope.

A stethoscope attachment 100 is an attachment to be mounted to a stethoscope 1 similarly to the foregoing stethoscope attachment 10 for enabling the operation for bringing the ear tube 3 into the state of expansion. As shown in FIG. 3, the stethoscope attachment 100 comprises a pair of manipulation unit 112 (each also called hereunder when required a left manipulation part 114 and a right manipulation part 116) and a hinge 118. And the stethoscope attachment 100 is different in structure from the above-mentioned stethoscope attachment 10 in that it is provided with a mounting member 130 for mounting the left and the right manipulation part 114, 116 to the left and the right tube part 3a, 3b.

The manipulation unit 112 (left manipulation part 114 and right manipulation part 116) is so structured as having amounting part 120 at one end and a manipulating part 122 at the other end. The manipulation unit 112 is formed by working a wire material (such as wire). The left and the right manipulation parts 114 and 116 are in a shape of substantially symmetric with each other.

The manipulation unit 112 is different, at the structure of the manipulating part 120, from the mounting part 20 forming the stethoscope attachment 10 of the foregoing first embodiment. In detail, the mounting part 120 is mounted along the left tube part 3a or the right tube part 3b similarly to the mounting part 20 but is different therefrom in the specific mounting structure. Specifically, the mounting part 20 is in a shape of being bent to be able to be mounted to the left or the right tube part 3a, 3b in a manner of being caught from the inside of the region X. Meanwhile, the mounting part 120 is different from the mounting part 20 in such structure that it is in a shape of extending straightly and employs a mounting member 130 for mounting the mounting part 120 to the left or the right tube part 3a, 3b.

The mounting part 120 in the state of being mounted to the stethoscope 1 has such length that it extends to reach a position more away toward the utmost end from a part of the left tube part 3a or the right tube part 3b covered with the connecting pipe 4. The mounting part 120 is mounted to the left or the right tube part 3a or 3b by means of amounting member 130 at a position more away toward the utmost end from a region of the left tube part 3a or the right tube part 3b covered with the connecting pipe 4. The mounting member 130 may employ a wire or the like in an annular shape, an annular member such as a clamping band, or a cylindrical member and be mounted as winding the outer peripheries of both of the left or the right tube part 3a or 3b and the mounting part 120 arranged along the left or the right tube part 3a or 3b.

The manipulating part 122 of the manipulation unit 112 is though different in shape from the manipulating part 22 forming the stethoscope attachment 10 in the foregoing first embodiment, it shows the same function. That is, the manipulating part 122 is provided on the manipulation unit 112 at the opposite position to the mounting part 120, and it is so structured that it can be hooked by user's fingers upon manipulation.

The hinge 118 is provided at an intermediate position between the mounting part 120 forming the left and the right manipulation unit 114, 116 and the manipulating part 122. And the hinge 118 connects the left and the right manipulation parts 114 and 116 in a manner of enabling the same to be operated opened and closed. The hinge 118 is structured similarly to the foregoing hinge 18 in such manner that a fulcrum shaft 124 made from a combination of bolt and nut or the like is inserted through a hole-like part provided by looping a wire material which forms the left manipulation part 114 and the right manipulation part 116.

The stethoscope attachment 100 does, similarly to the foregoing stethoscope attachment 10, function such that the manipulating parts 122 are held by users with their fingers to cause the interval between the manipulating parts 122 to narrow, thereby enabling expansion of the interval between the manipulating parts 120 of the left and the right manipulation parts 114, 116 (expansion operation). By carrying out the expansion operation, it is enabled to expand the interval between the left and the right tube parts 3a, 3b. Besides, by making lower the holding force holding (with fingers) the manipulating parts 122, the interval between the left tube part 3a and the right tube part 3b can be returned to the state not subjected to an external force. Thus, the stethoscope attachment 100 also may be used to realize that users such as doctors or the like can attach and detach the stethoscope 1 with a single hand. Also, the above-mentioned stethoscope attachment 100 may be attached for use to any stethoscope 1 freely selected by the doctors or the like.

Furthermore, in the stethoscope attachment 100, the mounting part 120 is mounted to the left tube 3a or the right tube part 3b by use of the mounting part 130 at a position away toward the utmost end from the region of the left tube part 3a or the right tube part 3b covered by the connecting pipe 4. Thus the mounting part 120 contacts with the left or the right tube part 3a, 3b at their sections being exposed, so that the mounting part 120 is subjected to low sliding resistance at the mounting position in comparison with the foregoing stethoscope attachment 10. Thus the mounting part 120 is able to readily slide along the left or the right tube part 3a, 3b. By this structure, load required for holding (with fingers) the manipulating part 122 upon carrying out the expansion operation can be lowered. Hence, according to the stethoscope attachment 100, the expansion operation bringing the ear tube 3 into the expansion state can be carried out more lightly.

Figure 5:
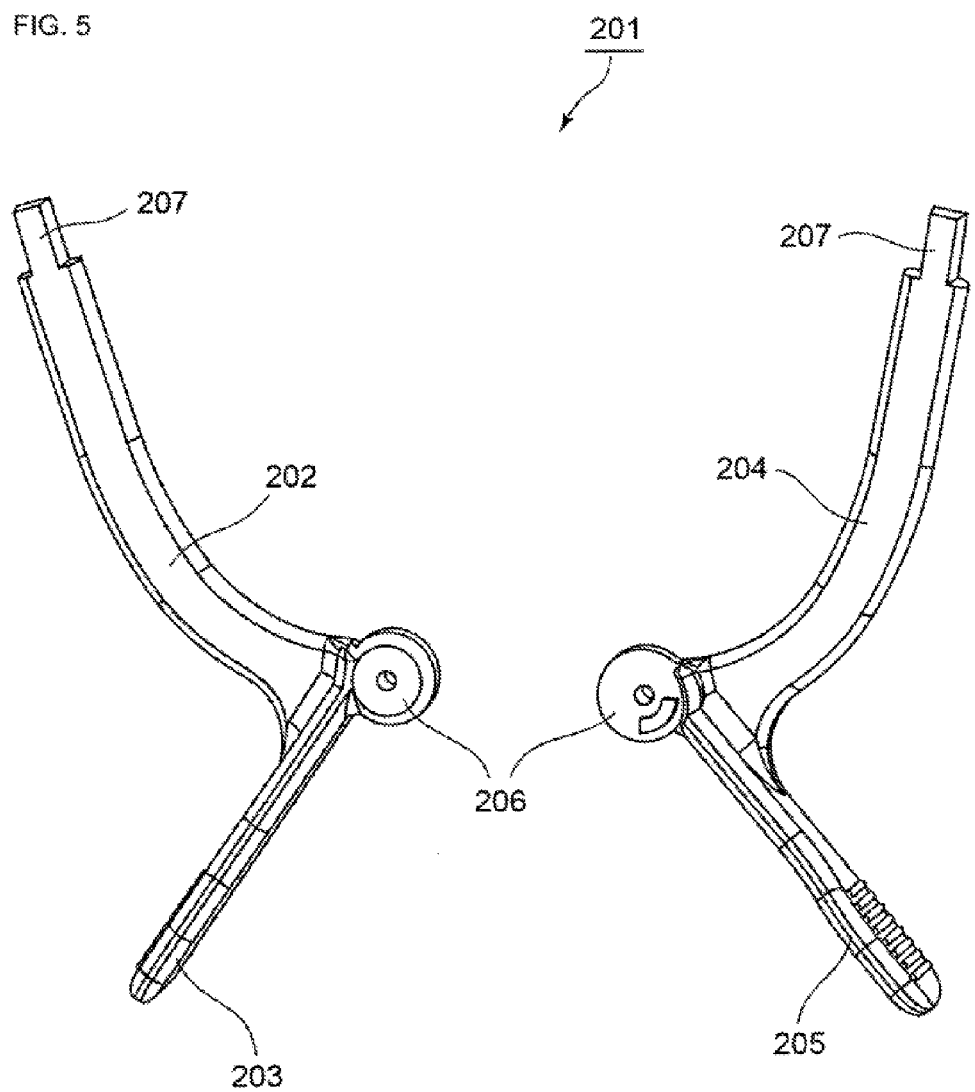
FIG. 5: a front view showing further other example of an attachment for stethoscope according to the present invention in the state of before assembling.

FIG. 5 is a front view showing further other example of the stethoscope attachment 201 according to the present invention in the state of being not assembled. In this example, the whole of the attachment 201 is made of plastic. The left manipulation part 202 and the left manipulating part 203 are formed in a manner of being unified and having a through bore part 206 centrally. Also, the right manipulation part 204 and the left manipulating part 205 are formed in a manner of being unified and having a through bore part 206 centrally. A shaft member is provided to be inserted through the through bore of the through bore part 206 in a manner of enabling rotation.

Figure 6:
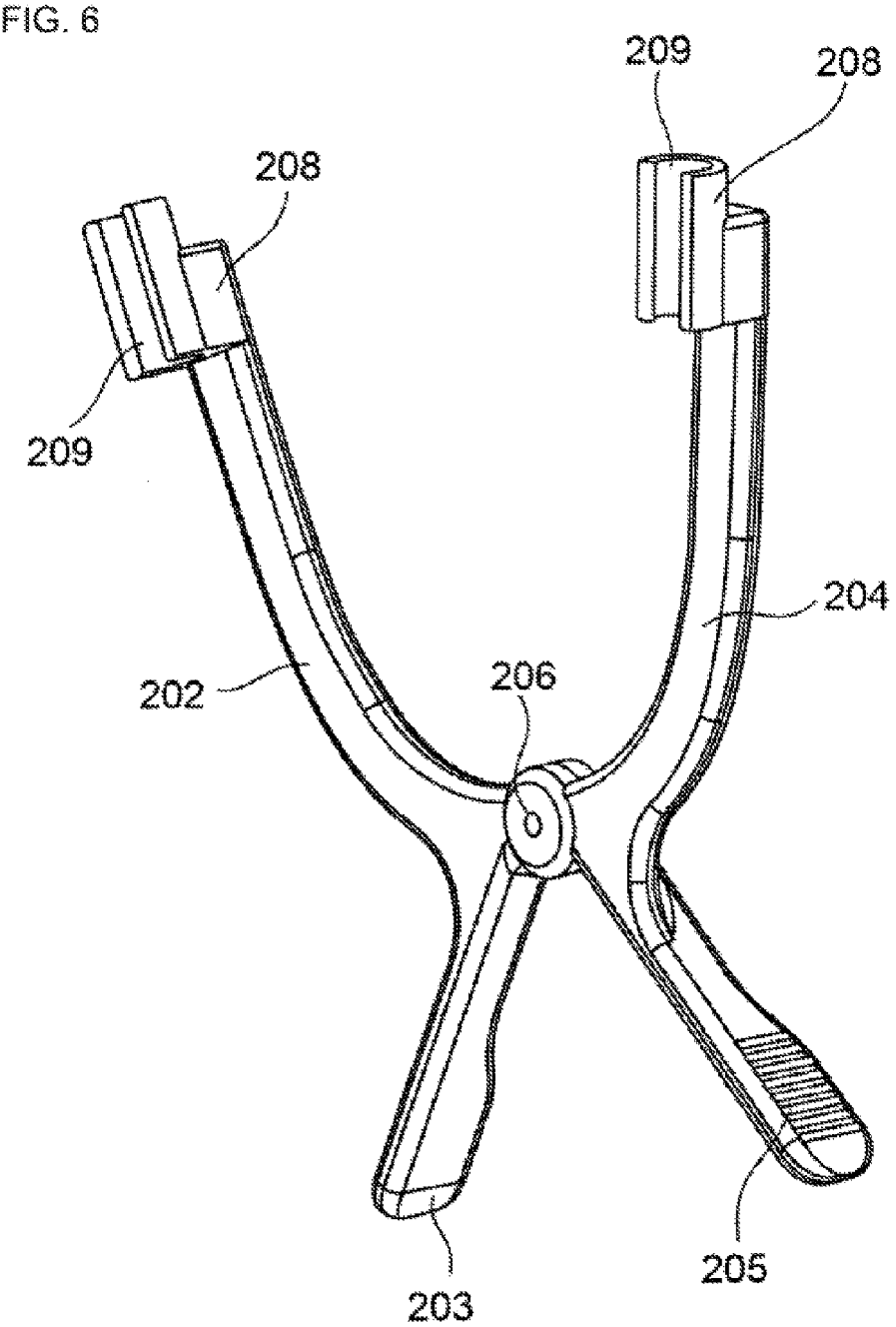
FIG. 6: a perspective view showing the example shown in FIG. 5 with the through bore parts assembled with a shaft fit into it to be able to rotate.

The end 207 of the manipulation part 202, 204 is smaller in width a little in this example (such feature though not indispensable). FIG. 6 shows the state of the through bore parts 206 assembled, with a shaft member being inserted, to be rotatable. Besides, fixed at the end part 207 of the manipulation part is a grasping means 208 which is to be fit and fixed to the ear tube 3 of the stethoscope. The ear tube 3 may be fit in a groove 209 formed on the grasping means 208. Otherwise, the connecting pipe 4 may be fit in the groove 209 depending upon the size of the groove 209.

The grasping means 208 may be subjected, at the groove 209, to anti-slipping working, such as making concave and convex, applying rubber, or the like. Furthermore, an anti-slipping means separate from the grasping means 208 may be fixed to the ear tube 3. And the anti-slipping means may be provided with a screw or the like to be tightened.

Figure 7:
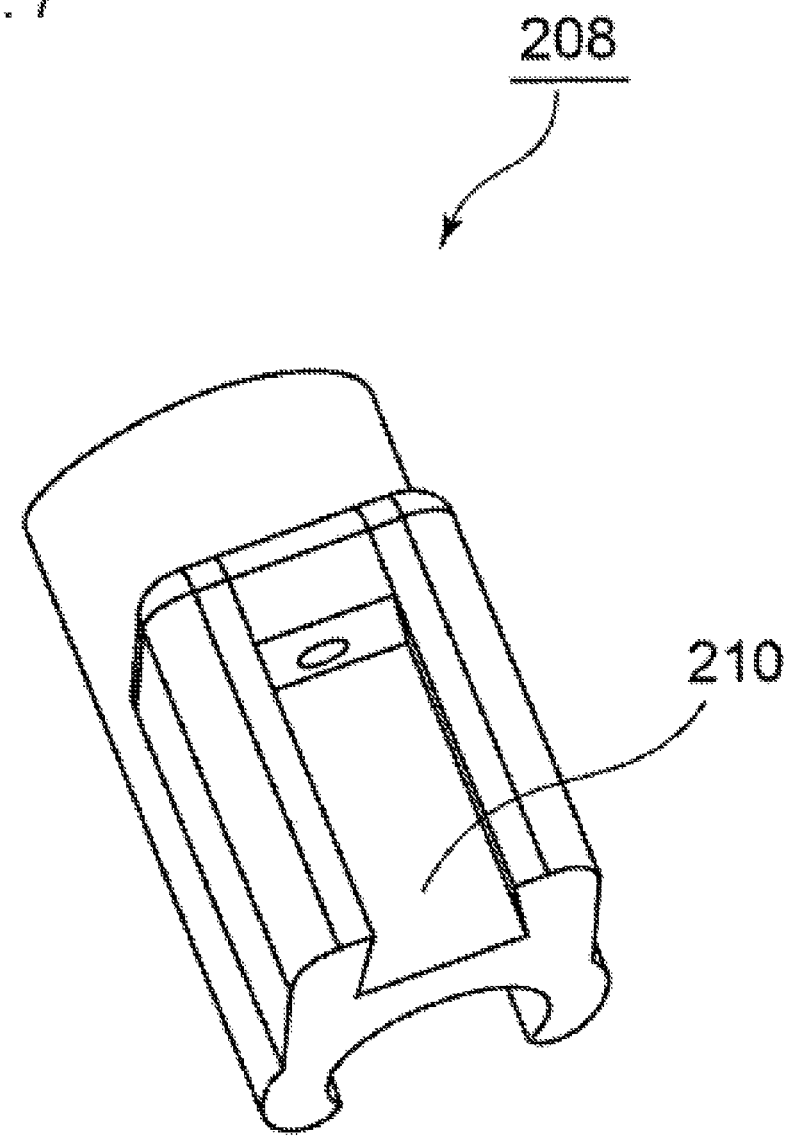
FIG. 7: a perspective view of the grasping member shown in FIG. 6.

FIG. 7 is a perspective view of the grasping means 208 shown in FIG. 6. The grasping means 208 has a recess 210 (into which the end part 207 is inserted) and the groove 209 at the opposite side. The grasping means 208 enables readily fixing to the ear tube.

Figure 4:
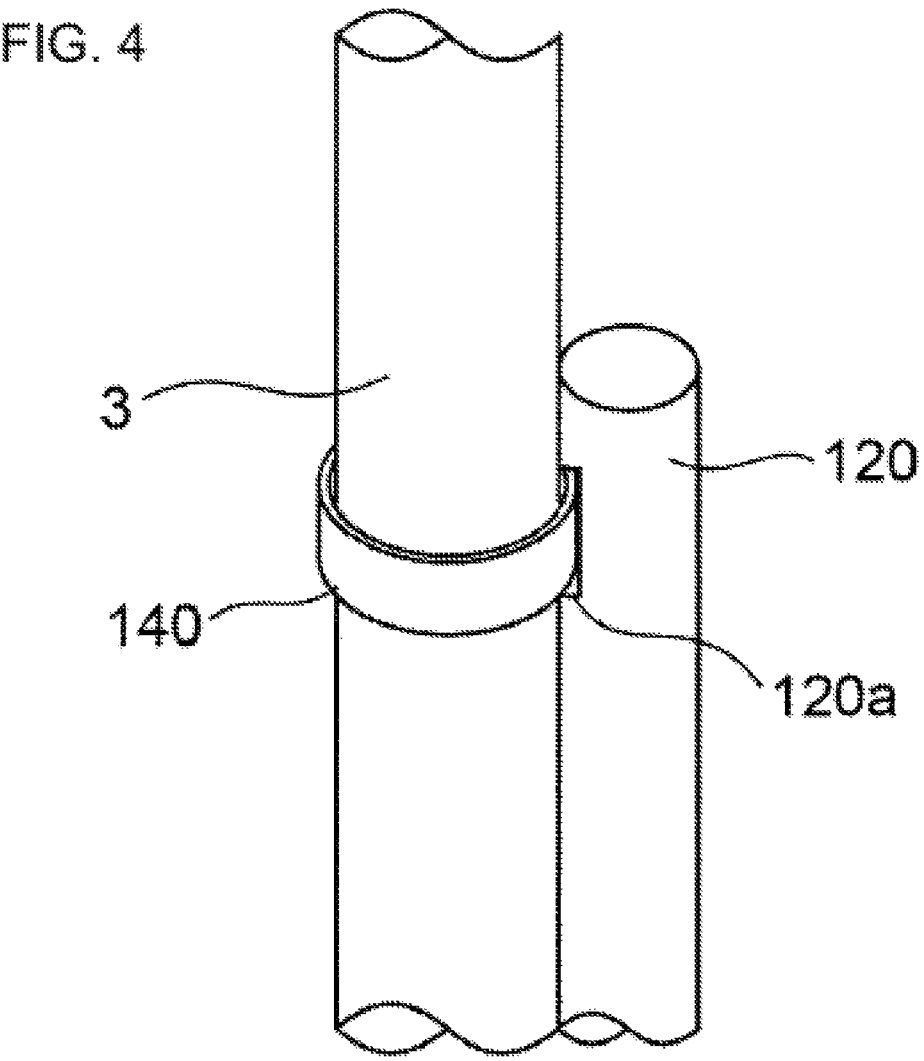
FIG. 4: a perspective view showing an example of modification of the mounting structure for the attachment for stethoscope shown in FIG. 3.

Hereby the specific embodiments of the present invention have been explained with referring to the attached drawings. But, it will be appreciated that concrete structures should not be limited to those mentioned embodiments. Scope of the present invention shall be expressed with the patent claims but not with the foregoing explanation of the embodiments. And the scope of the present invention shall cover all modification within equivalent meanings and extent to the patent claims. For example, in the second embodiment, the example is shown that the mounting part 120 in an almost straightly extending wire-like or bar-like shape is arranged along the left or the right tube part 3*a* or 3*b* and a mounting member 130 is mounted as winding around the outer peripheries of the mounting part 120 and the left or the right tube part 3*a* or 3*b*. The structure for mounting the mounting part 120 is not limited to this. Specifically, as shown in FIG. 4, the mounting part 120 may be provided with an insertion bore 120*a* and an annular member 140 in an annular shape is prepared similarly to the mounting member 130. And the annular member 140 is inserted through the insertion bore 120*a* and is mounted as winding around the left or the right tube part 3*a* or 3*b*. By this, the mounting part 120 is enabled to be mounted more securely to the left or the right tube part 3*a* or 3*b*.

Also, in the manipulating part 22 of the first embodiment and that 122 of the second embodiment, a cover made of a flexible material such as rubber may be fit on the surface. By this, the manipulating part, upon manipulation of the stethoscope attachment, can be prevented from catching fingers of users hands, whereby providing a stethoscope attachment readily operated by users.

INDUSTRIAL APPLICABILITY

The attachment for stethoscope of the present invention is usable for every existing stethoscopes freely selected by users.

REFERENCE SIGNS LIST

1: stethoscope
2: sound collecting unit
3: ear tube
3*a*: the left tube part,
3*b*: the right tube part
4: connecting pipe
10, 100: attachment for stethoscope
12, 112: manipulation unit
14, 114: left manipulation part
16, 116: right manipulation part
18, 118: hinge
20, 120: mounting part
22, 122: manipulating part
24, 124: fulcrum shaft
130: mounting member
140: annular member
201: attachment for stethoscope of the present invention
202: left manipulation part
203: left manipulating part
204: right manipulation part
205: left manipulating part
206: through bore part
207: end part
208: grasping means
209: groove
210: recess

The invention claimed is:

1. An attachment for stethoscope to be mounted to a stethoscope comprising: a sound collecting unit for detecting the auscultation sounds, an ear tube branched into a left tube part and a right tube part having ear pieces at the utmost ends so as to be inserted into the left and right ears of a user, and a connecting pipe which connects the sound collecting unit and the left tube part and the right tube part, characterized in that the attachment for stethoscope comprises:
   a mounting part to be mounted to the ear tube,
   a manipulating part for manipulating the mounting part, and
   a hinge to which the manipulating part and the mounting part are connected in a manner of being capable of rotating, so that the mounting part may be opened and closed by opening and closing operation of the manipulating part and upon the attachment's being fit to the stethoscope the hinge is positioned outside a region surrounded by the left tube part and the right tube part, and the connecting pipe, such that the hinge is on an opposite side of the ear pieces relative to a point of connection between the left and right tubes.

2. The attachment for stethoscope as set forth in claim 1 wherein the left section of the mounting part is formed in a manner of being unified with the left section of the manipulating part, and the right section of the mounting part is formed in a manner of being unified with the right section of the manipulating part, and the unified left sections of the mounting part and the manipulating part and the unified right sections of the same are connected by means of a rotatable hinge.

3. The attachment for stethoscope as set forth in claim 1 wherein the left section of the mounting part is formed in a manner of being unified with the right section of the manipulating part, and the right section of the mounting part is formed in a manner of being unified with the left section of the manipulating part, and the unified left and right sections of the mounting part and the manipulating part and the unified right and left sections of the mounting part and the manipulating part are connected by means of a rotatable hinge.

4. The attachment for stethoscope as set forth in claim 1 wherein a part of the mounting part has a structure as being able to be mounted to the ear tube.

5. The attachment for stethoscope as set forth in claim 1 wherein the mounting part and the ear tube are fixed to each other by use of a separately provided mounting and tightening member.

6. The attachment for stethoscope as set forth in of claim 1 wherein a stopper is provided at a rotating part of the hinge to prevent the mounting part from withdrawing more than a predetermined extent.

7. The attachment for stethoscope as set forth in claim 1 wherein such expansion operation is able to be carried out that operation is made to cause the left section of the manipulating part and the right section of the manipulating part to approach each other, so that the interval between the left section of the mounting part and the right section of the mounting part is expanded, the mounting part having a section in a hook-like shape bent along the outer peripheries of the left tube part and the right tube part, or of the left tube part and the right tube part covered with ends of the connecting pipe at the side of the ear tube, in the state that the mounting part is mounted to the left tube part and the right tube part, or the left tube part and the right tube part covered with ends of the connecting pipe at the side of the ear tube, the expansion operation is carried out to enable the ear tube to be brought into expansion state.

8. The attachment for stethoscope as set forth in claim 7 characterized in that at the outside of a region surrounded by the left tube part, the right tube part, and the connecting pipe, the attachment comprises a pair of left manipulation part and right manipulation part in a shape of being capable of being mounted along the left tube part and the right tube part, one end of the left manipulation part is connected with one end of the right manipulation part through a fulcrum shaft, so that operation is carried out to cause the left section of the manipulating part and the right section of the manipulating part to approach each other, whereby the left manipulation part and the right manipulation part interlock, thereby enabling expansion operation that the interval between the left section of the mounting part and the right section of the mounting part is expanded.

9. The attachment for stethoscope as set forth in claim 8 characterized in that the attachment for stethoscope is made of plastic, and the left manipulation part and the right manipulation part are formed in a shape of being made more narrowed at a part nearer the utmost end.

10. The attachment for stethoscope as set forth in claim 9 characterized in that the manipulating part is subjected to anti-slipping working, such as having concave and convex.

11. The attachment for stethoscope as set forth in claim 9 characterized in that the hook-like shaped section is subjected to anti-slipping working.

12. The attachment for stethoscope as set forth in claim 1 wherein such expansion operation is able to be carried out that operation is made to cause the left section of the manipulating part and the right section of the manipulating part to approach each other, so that the interval between the left section of the mounting part and the right section of the mounting part is expanded, the attachment comprising an annular member to be used for mounting one or both of the left section and the right section of the mounting parts to the left tube part or the right tube part, or, the left tube part and the right tube part covered with ends of the connecting pipe at the side of the ear tube, so that in the state that the mounting parts are mounted to the left tube part and the right tube part, or, the left tube part and the right tube part covered with ends of the connecting pipe at the side of the ear tube, the expansion operation is carried out to bring the ear tube into the expansion state.

13. The attachment for stethoscope as set forth in claim 12 characterized in that at the outside of a region surrounded by the left tube part, the right tube part, and the connecting pipe, the attachment comprises a pair of left manipulation part and right manipulation part in a shape of being capable of being mounted along the left tube part and the right tube part, one end of the left manipulation part is connected with one end of the right manipulation part through a fulcrum shaft, so that operation is carried out to cause the left section of the manipulating part and the right section of the manipulating part to approach each other, whereby the left manipulation part and the right manipulation part interlock, thereby enabling expansion operation that the interval between the left section of the mounting part and the right section of the mounting part is expanded.

14. The attachment for stethoscope as set forth in claim 13 wherein the mounting part is provided, at the side of the ear tube, with an insertion part through which the annular member is inserted, so that the annular member is inserted through the insertion part and is mounted as winding around the left or the right tube part, whereby, one or both of the mounting parts of the left manipulation part and the right manipulation part is/are enabled to be mounted to the left or the right tube part.

* * * * *